United States Patent [19]

Eaton, II

[11] 4,253,831
[45] Mar. 3, 1981

[54] ASPIRATING DENTAL DEVICE

[76] Inventor: Melvin H. Eaton, II, 2600 W. Landing Rd., Virginia Beach, Va. 23456

[21] Appl. No.: 43,569

[22] Filed: May 29, 1979

[51] Int. Cl.³ .......................................... A61C 17/04
[52] U.S. Cl. ..................................... 433/91; 433/116
[58] Field of Search .................... 433/91, 95, 116, 92, 433/82

[56] References Cited

U.S. PATENT DOCUMENTS

| 3,208,145 | 9/1965 | Turner | 433/95 |
|---|---|---|---|
| 3,512,258 | 5/1970 | Johnson | 433/91 |
| 3,526,219 | 9/1970 | Balamuth | 433/91 |

Primary Examiner—Robert Peshock
Attorney, Agent, or Firm—Beveridge, De Grandi, Kline & Lunsford

[57] ABSTRACT

An aspirating dental device. An elongated sleeve member extends along a dental instrument to define an airflow passage having an inlet, adjacent the working end of the dental instrument, and an outlet. A vacuum source is connected to the airflow passage to cause air to flow therethrough, drawing water and waste with it. The sleeve member can extend over the dental instrument to define the airflow passage between the exterior surface of the dental intrument and the interior surface of the sleeve member. In such case, the sleeve member can be cut to provide a hinged cover portion openable to permit access to the working end of the dental instrument, for example for installation or removal of a dental bur. Alternatively, the sleeve member can extend along and contact a portion of the exterior surface of the dental instrument to define the airflow passage therebetween. As another alternative, the sleeve member can be a tube extending along the dental instrument. In each of these embodiments, the sleeve member is readily removable for sterilization by an autoclave or other effective hygenic technique, while the dental instrument is sterilized with alcohol or other disinfecting agent in conventional manner, thus minimizing the possibility of transfer of infectious organisms. As another embodiment, the sleeve member can define the exterior of the dental instrument itself, with the airflow passage therein. The dental instrument can be a dental handpiece, a laser device, an electrosurgical device, an ultrasonic scaler or any other hard or soft tissue preparation or treatment device.

12 Claims, 7 Drawing Figures

ASPIRATING DENTAL DEVICE

BACKGROUND OF THE INVENTION

The present invention pertains to an aspirating dental device. More particularly the present invention pertains to an aspirating dental device incorporating a dental instrument to remove liquid, gaseous fumes and waste as a dental procedure is being performed.

Numerous dental procedures result in generation of liquid and other waste which must be removed from the area in which the procedure is being performed. By way of example, during the treatment of teeth for removal of decay, the dentist frequently has occasion to work for extended periods in the mouth of the patient in the vicinity of the teeth undergoing treatment, and during such treatment the patient frequently salivates, resulting in accumulation of considerable saliva in the patient's mouth. This saliva must be removed, both to assure the dentist proper visibility of and access to the area undergoing treatment and to assure the patient's comfort. Additionally, many dental handpieces use a high speed dental bur onto which water or other liquid flows to remove the waste material from the vicinity of treatment as the bur operates and to maintain the area at a reasonable temperature. This water likewise must be removed from the mouth of the patient.

It is essential that any instrument used in a patient's mouth, and capable of retaining bacteria from the patient's oral cavity, be thoroughly disinfected or be discarded after use to prevent subsequent contamination or infection of another patient. Proper disinfecting usually involves soaking of the instrument in a disinfectant or an autoclave, which requires thirty minutes or more.

Aspirating devices are known which withdraw liquid and other waste material from the mouth of a patient as the patient is undergoing dental treatment. Such devices generally also remove dust and waste particles of prepared teeth, metal restorations, porcelain and plastic, along with bacteria and other potentially harmful debris. The devices frequently operate by means of suction to remove loose material, thus avoiding exposure of the dentist or other operators to these potentially harmful byproducts that are normally thrown in the air by the action of the dental handpiece.

One commonly utilized form of aspirating device includes a small hooked tube which rests in the patient's mouth as the dentist works in the mouth with a dental instrument. While such an aspirating device is capable of removing liquids from the mouth of the patient, its inlet is generally located some small distance from the dental instrument and thus from the area undergoing treatment. As a consequence, it cannot assure thorough removal of liquid and other waste material from the vicinity in which the dentist is working. Additionally, such an aspirating device can result in some amount of discomfort for the patient.

U.S. Pat. No. 3,208,145 shows an aspirating dental handpiece providing water, air, and suction from a single instrument. While this device compactly provides three requirements of the dentist, still it leaves the aspirating inlet removed from the vicinity of the instrument during many dental procedures. U.S. Pat. No. 2,812,765 likewise shows an aspirating device incorporating both a fluid source and an aspirator in a single instrument. It, too, leaves the aspirating inlet removed from the vicinity of the dental instrument during dental procedures. U.S. Pat. No. 1,390,354 shows a dental grinding wheel having an aspirating hood. Essentially, the aspirating hood is similar to a small vacuum cleaner attachment mounted over the grinding wheel. The device suffers from a significant shortcoming in that it is difficult to thoroughly sterilize it. Provision must be made in any such device to assure that liquid, such as saliva from a patient, does not drain from the device into the mouth of a later patient. Thus, the device must be thoroughly sterilized between patients and so it must be easily removable from the dental instrument. Because of its size this device also interferes with the densist's view of the area undergoing treatment. U.S. Pat. No. 3,512,258 shows a shroud for fitting on a dental instrument such as a dental prophylaxis angle to permit attachment of an aspirating tube thereto. Problems of sterilization still exist, and the aspirating tube is positioned in such a manner that it interferes with the dentist's view of the area undergoing treatment.

U.S. Pat. No. 3,092,908 shows an aspirating dental drill in the form of a turbine powered bur. A vacuum source is connected to one end of the device to draw air into it. This air drives a turbine which operates the dental bur. The vacuum source is also intended to draw liquid and other extra fine waste material from the mouth of the patient. This device appears to have numerous shortcomings. Thus, if there is a significant quantity of saliva or other liquid in the mouth of the patient, which the device is to remove, the airflow is reduced, thereby reducing the speed at which the dental bur is driven. Additionally, the device draws the extra fine waste material immediately past the turbine, with its delicate mounting. The dust which results from dental procedures is extremely abrasive, and as a consequence, considerable wear would be experienced on the moving parts of this device. Further, the device includes a screen over its inlet end, and the dust and other waste material is likely to clog the screen, thereby further reducing the flow of air and so the speed of the turbine-driven dental bur. Most significantly, the device will suck fluids from the mount of the patient and thus requires thorough sterilization before use on another patient. Since the aspirating device is incorporated into the entire drive system for the dental bur, it is not possible to sterilize the drive system during the brief interval between consecutive patients.

SUMMARY OF THE INVENTION

The present invention is an aspirating dental device overcoming these several shortcomings of such prior art devices and providing the dentist with a device incorporating the aspirating inlet and the working instrument in a unitary, compact dental device. In accordance with the present invention, an elongated sleeve member extends along a dental instrument, which has a working end, to define an airflow passage having an inlet, adjacent the dental instrument working end, and an outlet. Means such as a vacuum source is connected to the airflow passage outlet to provide vacuum to the airflow passage to draw air therethrough from the inlet to the outlet, drawing liquid and other waste matter with the air. In one preferred embodiment of the present invention, the sleeve member is in the form of a hollow sleeve extending over the dental instrument to define the airflow passage between the exterior surface of the dental instrument and the interior surface of the sleeve member. Not only does this sleeve member define the airflow passage, but also it aids in muffling the sound of the air driven dental handpiece. The sleeve member can be made, for example, from a molded polyvinyl chloride, but other suitable materials might be used. Preferably, a cut is provided in the sleeve member to form a hinged cover portion openable to permit access to the working end of the dental instrument within the sleeve member, although this is not essential to the concept of the invention. Thus, when the dental instrument is a dental handpiece, this hinged cover portion permits installation and removal of a dental bur without having to remove the sleeve member from its position over the dental handpiece.

In another preferred embodiment of the present invention, the sleeve member extends adjacent a portion of the exterior surface of the dental instrument to define the airflow passage between that portion of the exterior surface of the dental instrument and the interior surface of the sleeve member. In a third embodiment of the present invention, the sleeve member takes the form of an elongated hollow tube member extending along the exterior surface of the dental instrument. In yet another embodiment, the dental instrument is incorporated within the sleeve member to use the sleeve member as its housing.

BRIEF DESCRIPTION OF THE DRAWINGS

These and other aspects and advantages of the present invention are more apparent in the following detailed description and claims, particularly when considered in conjunction with the accompanying drawings in which like parts bear like reference numerals. In the drawings:

DETAILED DESCRIPTION OF A PREFERRED EMBODIMENT

Figure 1:
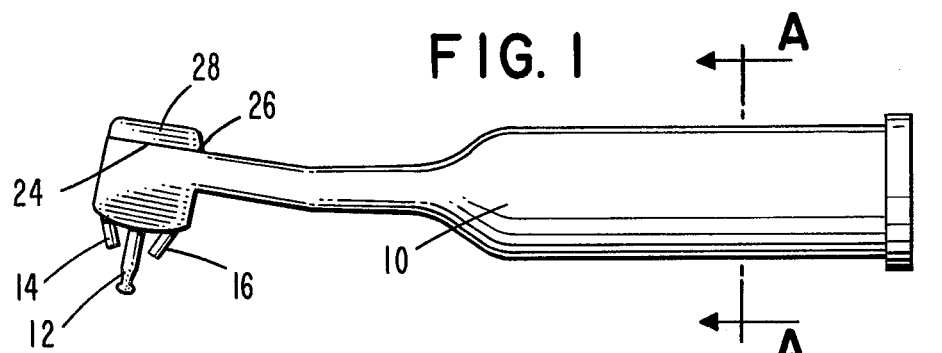
FIG. 1 is a side elevational view illustrating a dental device in accordance with the present invention.
Figure 2:
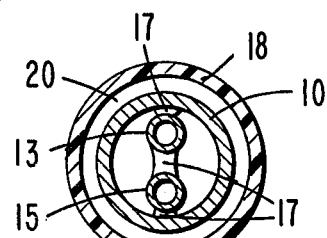
FIG. 2 is an enlarged sectional view taken along line A—A of FIG. 1 and depicting a first embodiment of a dental device in accordance with the present invention.
Figure 3:
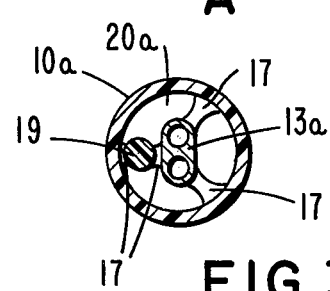
FIG. 3 is a sectional view taken along line A—A of FIG. 1 and depicting a second embodiment of dental device in accordance with the present invention.

FIG. 1 illustrates a dental device in accordance with the present invention, and FIGS. 2 and 3 depict two different embodiments of that dental device. Looking first at FIGS. 1 and 2, an embodiment of the present invention suitable for use in conjunction with a standard dental handpiece is shown. Dental handpiece 10 (FIG. 2) is a conventional dental handpiece used, for example, for removal of decayed material from a tooth in preparation of the tooth for restoration. A dental bur 12 is installed in the working end of dental handpiece 10 during numerous dental procedures. A first tube 13 for compressed air and a second tube 15 for water extend within handpiece 10 and are held in position by spider members 17. An outlet 14 for water is generally provided at the working end of handpiece 10. A Fiberoptic Type light source 16 might also be incorporated in the working end of handpiece 10.

Dental handpiece 10 with bur 12, tubes 13 and 15, outlet 14, and light source 16 is a conventional dental handpiece. An elongated hollow sleeve member 18 is fitted over dental handpiece 10 and defines an airflow passage 20 between the exterior surface of handpiece 10 and the interior surface of sleeve member 18. While handpiece 10 can be freely positioned within sleeve member 18, if preferred, a number of ridges or bumps can be molded at intervals on the interior surface of sleeve member 18 to retain handpiece 10 somewhat centrally positioned within the sleeve member. Adjacent the second end of dental handpiece 10, sleeve member 18 is adapted, by means of a threaded attachment, friction attachment, or otherwise, for connection to a vacuum source. Thus, when the vacuum source is activated, air flows from the inlet end of the airflow passage adjacent the working end of the dental handpiece, through airflow passage 20, to the outlet end of the airflow passage, bringing with it liquid and other waste material from the vicinity of dental bur 12.

Preferably, in this embodiment of the dental device of the present invention in which the sleeve member fits over a standard dental handpiece, a cut 24 is formed through the sleeve member adjacent the surface of the working end of the dental handpiece opposite that in which the dental bur is installed. This cut extends to define a hinge portion 26, permitting cover 28 to be pivotably moved to expose the surface of the dental handpiece, allowing installation and/or removal of a dental bur without removal of sleeve member 18 from dental handpiece 10. Cover 28 can be formed with a snap fit or other appropriate latch to retain it in its closed position, while permitting ready opening when desired.

In operation, the vacuum source connected to the second end of tube 18 is activated, and compressed air and water are provided through tubes 13 and 15, as desired. The dentist utilizes the handpiece in the conventional manner, and the vacuum source draws the waste water and other waste material through airflow passage 20, keeping the area adjacent dental bur 12 free from water and other waste material. If desired, sleeve 18 can fit more closely about a portion of dental handpiece 10 than about the remainder thereof to increase the air velocity therethrough. When the dental work has been completed and a new patient is to be handled, the vacuum source is turned off, and sleeve member 18 is slid off the dental handpiece. Handpiece 10 is then sterilized with alcohol or other disinfectant in conventional manner, while sleeve member 18 is sterilized, for example in an autoclave, or discarded. A previously sterilized sleeve member is then installed on handpiece 10 in preparation for the next patient. Accordingly, the dental device of the present invention is readily sterilized.

In a dental device in accordance with the present invention, a dental instrument can be housed directly and permanently in the airflow-passage-defining sleeve, as depicted in the embodiment of the present invention illustrated by FIGS. 1 and 3. Dental handpiece 10a surrounds tube 13a which incorporates into a single member the compressed air and water tubes 13 and 15 of FIG. 2, and airflow passage 20a is defined between the interior surface of handpiece 10a and the exterior surface of tube 13a. FIG. 3 also illustrates a fiber optic light carrying member 19 within the dental device which terminates at the working end to provide a light source in the area undergoing treatment. With this form of dental device, the entire device must be sterilized in an autoclave or other appropriate disinfecting means.

Figure 4:
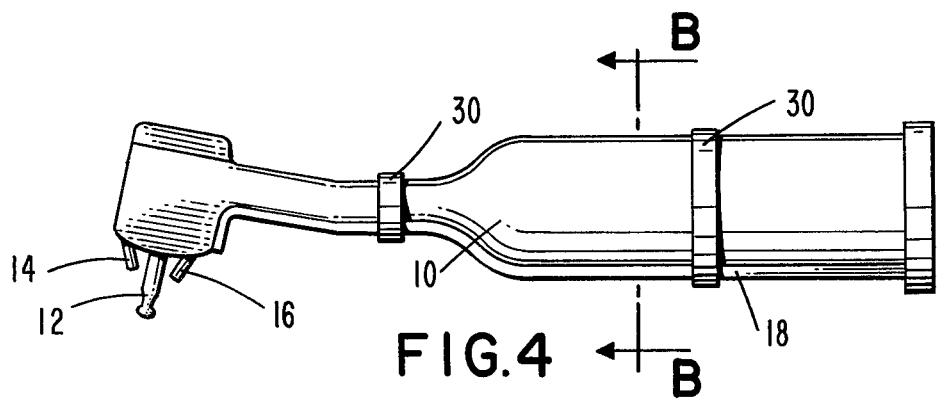
FIG. 4 is a side elevational view likewise illustrating a dental device in accordance with the present invention.
Figure 5:
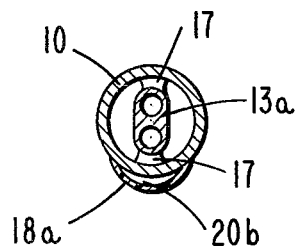
FIG. 5 is a sectional view taken along line B—B of FIG. 4 and depicting another embodiment of dental device in accordance with the present invention.
Figure 6:
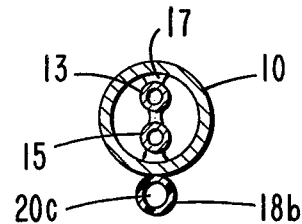
FIG. 6 is a sectional view taken along line B—B of FIG. 4 and depicting a further embodiment of dental device in accordance with the present invention.

FIGS. 4 and 5 depict another form of the present invention. Elongated sleeve member 18a extends along the lower surface of dental handpiece 10 and is held in place, for example, by clip-on or elastic retaining members 30. In the embodiment depicted in FIG. 5, sleeve 18a is formed of a section of material tightly fitting against a portion of the outer surface of handpiece 10 to define the airflow passage 20b between that portion of the outer surface of handpiece 10 and the interior surface of sleeve member 18a. In the embodiment depicted in FIGS. 4 and 6, the elongated sleeve member 18b is formed as an elongated hollow tube member which extends along the exterior surface of handpiece 10, and airflow passage 20c is defined within tube member 18b. With these forms of dental device, when it is desired to sterilize the equipment, retaining members 30 are released, and the elongated sleeve member 18 is removed and is placed in an autoclave or other sterilization device or is discarded, while dental handpiece 10 is sterilized with alcohol or other disinfectant in conventional manner.

Figure 7:
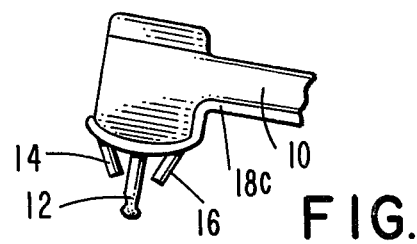
FIG. 7 is a fragmentary side elevational view depicting another embodiment of dental device in accordance with the present invention.

FIG. 4 depicts elongated sleeve member 18 terminating at an inlet adjacent one portion of the working end of dental handpiece 10. FIG. 7 depicts a variation in which the elongated sleeve 18c extends around the circumference of the working end of handpiece 10 to provide the inlet end of the airflow path around that entire circumference.

The dental device of the present invention incorporating an elongated sleeve member to define an airflow path is not limited to use in conjunction with a dental handpiece. Thus, such a sleeve member can be utilized with any tooth or tissue preparation or treatment means, including laser, electrosurgical and ultrasonic scaler. Thus, although the present invention has been described with reference to preferred embodiments, numerous alterations, rearrangements, and substitutions can be made, and still the result will come within the scope of the invention.

What is claimed is:

1. An aspirating dental device comprising:
   an elongated sleeve member adapted to extend along an operative dental handpiece having a working end while being spaced therefrom, to define an air flow passage having an inlet adjacent the dental instrument working end and an outlet, said sleeve member being readily removable therefrom; and
   means connected to said air flow passage outlet and adapted for connection to a vacuum source for providing suction to said airflow passage to cause air to be removed therethrough from said inlet to said outlet whereby during use said sleeve member provides a passage for suction of fluids and wastes from adjacent the dental handpiece working end and after use the sleeve member can be removed to permit sterilization of the dental handpiece.

2. A dental device as claimed in claim 1 in which said sleeve member comprises a hollow sleeve member adapted to extend over the dental handpiece to define the airflow passage between the exterior surface of the dental handpiece and the interior surface of said sleeve member.

3. A dental device as claimed in claim 2 further comprising a dental handpiece within said sleeve member.

4. A dental device as claimed in claim 1 in which said sleeve member is adapted to extend adjacent a portion of the exterior surface of the dental handpiece to define the airflow passage between said portion of the exterior surface of said dental handpiece and the interior surface of said sleeve member.

5. A dental device as claimed in claim 4 further comprising a dental handpiece having said sleeve member extending adjacent a portion of the exterior surface thereof.

6. A dental device as claimed in claim 1 in which said sleeve member comprises a hollow tube member adapted to extend adjacent the exterior surface of the dental handpiece.

7. A dental device as claimed in claim 6 further comprising a dental handpiece having said hollow tube member extending along the exterior surface thereof.

8. A dental device as claimed in claim 1 further comprising a dental handpiece having said sleeve member extending therealong.

9. An aspirating dental device comprising:
   an elongated sleeve member adapted to extend over a dental instrument having a working end, to define an airflow passage between the exterior surface of the dental instrument and the interior surface of said sleeve member, said airflow passage having an inlet, adjacent the dental instrument working end, and an outlet, said sleeve member being cut to provide a hinged cover portion openable to permit access to the working end of a dental instrument within said sleeve member; and
   means connected to said airflow passage outlet and adapted for connection to a vacuum source for providing vacuum to said airflow passage to cause air to flow therethrough from said inlet to said outlet whereby during use said sleeve member provides a passage for suction of fluids and wastes from adjacent the dental handpiece working end and after use the sleeve member can be removed to permit sterilization of the dental handpiece.

10. A dental device as claimed in claim 9 further comprising a dental handpiece within said sleeve member.

11. A dental device as claimed in claim 10 in which said hinged cover portion permits installation of a dental bur in said dental handpiece.

12. An aspirating dental device comprising:
   an operative dental handpiece having a working end for removal and adjustment of relatively hard tooth tissues and surrounding tissues;
   an elongated sleeve member extending along the dental handpiece while being spaced therefrom to define an airflow passage having an inlet, adjacent said dental handpiece working end, and an outlet, the sleeve member being readily removable therefrom; and
   means connected to said overflow passage outlet and adapted for connection to a vacuum source for providing suction to said airflow passage to cause air to be removed therethrough from said inlet to said outlet whereby during use said sleeve member provides a passage for suction of fluids and wastes from adjacent the dental handpiece working end and after use the sleeve member can be removed to permit sterilization of the dental handpiece.

\* \* \* \* \*